(12) United States Patent
Jungwirth et al.

(10) Patent No.: US 9,863,890 B2
(45) Date of Patent: Jan. 9, 2018

(54) SOLAR CELL TESTING APPARATUS AND METHOD

(75) Inventors: Douglas R. Jungwirth, Reseda, CA (US); Emilio Quezada, Sylmar, CA (US); Gregory A. Campbell, Granada Hills, CA (US); James H. Ermer, Burbank, CA (US); Russell K. Jones, Manhattan Beach, CA (US)

(73) Assignee: The Boeing Company, Chicago, IL (US)

( * ) Notice: Subject to any disclaimer, the term of this patent is extended or adjusted under 35 U.S.C. 154(b) by 1357 days.

(21) Appl. No.: 13/157,826

(22) Filed: Jun. 10, 2011

(65) Prior Publication Data

US 2012/0313661 A1    Dec. 13, 2012

(51) Int. Cl.
  *G01R 31/26*     (2014.01)
  *G01N 21/95*     (2006.01)
  *H02S 50/10*     (2014.01)
  *G01N 21/66*     (2006.01)

(52) U.S. Cl.
  CPC ......... *G01N 21/9501* (2013.01); *H02S 50/10* (2014.12); *G01N 21/66* (2013.01)

(58) Field of Classification Search
  CPC ...... G01J 1/0411; G01J 1/0422; G01J 1/0437; G01J 1/0492; G01R 31/2656; H02S 50/10
  See application file for complete search history.

(56) References Cited

U.S. PATENT DOCUMENTS

| 4,043,668 A | * | 8/1977 | Goetz | G01J 3/32 |
| | | | | 250/339.04 |
| 4,564,808 A | * | 1/1986 | Faughnan | H02S 50/10 |
| | | | | 324/761.01 |
| 5,025,145 A | | 6/1991 | Lagowski | |

(Continued)

FOREIGN PATENT DOCUMENTS

| CN | 101419269 A | 4/2009 |
| CN | 101915859 A | 12/2010 |

(Continued)

OTHER PUBLICATIONS

Nagamine, F., et al., New Solar Simulator for Multi-Junction Solar Cell Measurements, Proceedings of the Photovoltaic Specialists Conference, Louisville, May 10-14, 1993, vol. 23, pp. 686-690.

(Continued)

*Primary Examiner* — Huy Q Phan
*Assistant Examiner* — Adam Clarke
(74) *Attorney, Agent, or Firm* — Charles L. Moore; Moore & Van Allen PLLC

(57) ABSTRACT

A solar cell testing apparatus may include an illuminator for directing light energy on a solar cell under test. The solar cell testing apparatus may also include a device for selectively positioning different filters of a multiplicity of filters in an optical path between the illuminator and the solar cell under test to at least one of measure performance and detect any defects in the solar cell. The multiplicity of filters may include a first set of filters and a second set of filters. Each filter of the first set of filters is adapted for passing a (Continued)

predetermined percentage of intensity of the light energy from the illuminator onto the solar cell under test. The second set of filters being adapted for testing the solar cell under different spectrums of light.

21 Claims, 7 Drawing Sheets

(56) References Cited

U.S. PATENT DOCUMENTS

| | | | | |
|---|---|---|---|---|
| 6,639,421 | B1* | 10/2003 | Yoshino et al. | 324/761.01 |
| 2004/0133086 | A1* | 7/2004 | Ciurczak | A61B 5/14546 |
| | | | | 600/322 |
| 2006/0126336 | A1* | 6/2006 | Solomon | F21S 10/007 |
| | | | | 362/277 |
| 2006/0214673 | A1 | 9/2006 | Tamai | |
| 2009/0279277 | A1* | 11/2009 | Jungwirth | F21S 8/006 |
| | | | | 362/2 |
| 2009/0297017 | A1* | 12/2009 | Hudgings et al. | 382/141 |
| 2010/0014080 | A1* | 1/2010 | Jungwirth et al. | 356/326 |
| 2011/0057113 | A1 | 3/2011 | Yokoi | |
| 2011/0116083 | A1* | 5/2011 | Mou | 356/233 |
| 2011/0227598 | A1 | 9/2011 | Park et al. | |
| 2011/0279810 | A1* | 11/2011 | Wang | G01N 21/55 |
| | | | | 356/72 |
| 2012/0010854 | A1* | 1/2012 | Ciocan et al. | 702/182 |
| 2012/0126120 | A1 | 5/2012 | Fuyuki et al. | |
| 2012/0138805 | A1* | 6/2012 | Missalla | G01J 1/0437 |
| | | | | 250/362 |

FOREIGN PATENT DOCUMENTS

| | | |
|---|---|---|
| CN | 102017190 A | 4/2011 |
| DE | 20 2008 014 0 36 U1 | 1/2009 |
| EP | 0 887 652 A2 | 12/1998 |
| JP | 2004273870 A | 9/2004 |
| JP | 2010278192 A | 12/2010 |
| JP | 201158953 A | 3/2011 |
| KR | 10-2005-0085408 | 8/2005 |
| WO | 2010/123189 A1 | 10/2010 |
| WO | 2011016441 A1 | 2/2011 |

OTHER PUBLICATIONS

European Patent Office, PCT International Search Report and the Written Opinion of the International Searching Authority for International Application No. PCT/US2012/038849 date of completion Sep. 6, 2012, dated Sep. 19, 2012, 13 pages.
Lansel, Steven, Technology and Future of III-V Multi-Junction Solar Cells, ECE 6542, Professor Chang, Aug. 21, 2005.
Japanese Patent Office; Office Action for Japanese Patent Application No. 2014-514479 dated Feb. 23, 2016, 3 Pages.
Chinese Patent Office; Office Action for Chinese Patent Application No. 201280028502.4 dated Nov. 16, 2015, 15 Pages.
Japanese Patent Office; Office Action for Japanese Patent Application No. 2014-514479 dated Jul. 4, 2016, 4 Pages.
Chinese Patent Office; Office Action for Chinese Patent Application No. 201280028502.4 dated Apr. 28, 2016, 18 Pages.
Chineses Patent Office; Office Action for Chinese Patent Application No. 201280028502.4 dated Nov. 9, 2016, 25 Pages.
Korean Intellectual Property Office; Office Action for Korean Patent Application No. 10-2013-7026372 dated Apr. 24, 2017, 10 Pages.
Nagamine, F., et al.; "New Solar Simulator for Multi-Junction Solar Cell Measurement," IEEE, 1993, pp. 686-690.
Chinese Patent Office; Office Action for Chinese Application No. 201280028502.4 dated Apr. 28, 2015, 17 pages.
Korean Intellectual Property Office; Office Action for Korean Patent Application No. 10-2013-7026372 dated Jul. 6, 2017, 6 Pages.
European Patent Office; Office Action for European Patent Application No. 12726523.9 dated Dec. 8, 2016, 7 Pages.

* cited by examiner

| FILTER/LOCATION | TEST PERFORMED* |
|---|---|
| ONE | FULL POWER |
| TWO | 50% POWER |
| THREE | 10% POWER |
| FOUR | TOP STARVED |
| FIVE | MIDDLE STARVED |
| SIX | BOTTOM STARVED |
| SEVEN | DARK I-V CURVE |
| EIGHT | ELECTRO-LUMINESCENCE |

SOLAR CELL TESTING APPARATUS AND METHOD

FIELD

The present disclosure relates to solar cells for converting light energy into electrical power, and more particularly to a solar cell testing apparatus and method of testing.

BACKGROUND

There are currently many initiatives for developing alternative forms of generating energy or renewable energy sources. One form of renewable energy or source for electrical power generation is photovoltaics or using a light source, such as the sun to generate electricity. Solar cells are photovoltaic devices which convert light energy or photons into electrical power. Mass production of individual solar cells and concentrator solar modules require optical testing to detect defects in the solar cells or concentrator solar modules and to measure performance of the solar cells. The optical testing typically requires illuminating the solar cells using a high intensity light source. However, existing tests are typically performed on various separate test stands and at low power levels. Additionally, current testing apparatus and procedures are inefficient and make it impractical to test 100% of solar cells or concentrator solar modules. Accordingly, there is a need for a more efficient and reliable apparatus and method for testing solar cells.

SUMMARY

In accordance with an embodiment, a solar cell testing apparatus may include an illuminator for directing light energy on a solar cell under test. The solar cell testing apparatus may also include a device for selectively positioning different filters of a multiplicity of filters in an optical path between the illuminator and the solar cell under test to at least one of measure performance and detect any defects in the solar cell. The multiplicity of filters may include a first set of filters and a second set of filters. Each filter of the first set of filters is adapted for passing a predetermined percentage of intensity of the light energy from the illuminator onto the solar cell under test. Each of the second set of filters is adapted for testing the solar cell under different spectrums of light.

In accordance with another embodiment, a solar cell testing apparatus may include an illuminator and a device for selectively positioning different filters of a multiplicity of filters in an optical path between the illuminator and a solar cell under test. The solar cell testing apparatus may also include a beam splitter. The beam splitter may direct a predetermined portion of the light from a selected filter of the multiplicity of filters onto the solar cell to at least one of measure performance and detect any defects in the solar cell. The beam splitter may also direct another predetermined portion of the light energy to an apparatus for measuring characteristics of the light from the selected filter of the multiplicity of filters positioned in the optical path between the illuminator and the solar cell.

In accordance with another embodiment, a method for testing a solar cell may include filtering light directed onto the solar cell by each of a multiplicity of filters to at least one of measure performance and detect any defects in the solar cell. The method may also include splitting the light to direct a predetermined portion of the filtered light onto the solar cell and to direct another predetermined portion of the light to an apparatus for measuring characteristics of the light from each of the multiplicity of filters.

Other aspects and features of the present disclosure, as defined solely by the claims, will become apparent to those ordinarily skilled in the art upon review of the following non-limited detailed description of the disclosure in conjunction with the accompanying figures.

BRIEF DESCRIPTION OF THE SEVERAL VIEWS OF THE DRAWINGS

The following detailed description of embodiments refers to the accompanying drawings, which illustrate specific embodiments of the disclosure. Other embodiments having different structures and operations do not depart from the scope of the present disclosure.

DESCRIPTION

Figure 1:
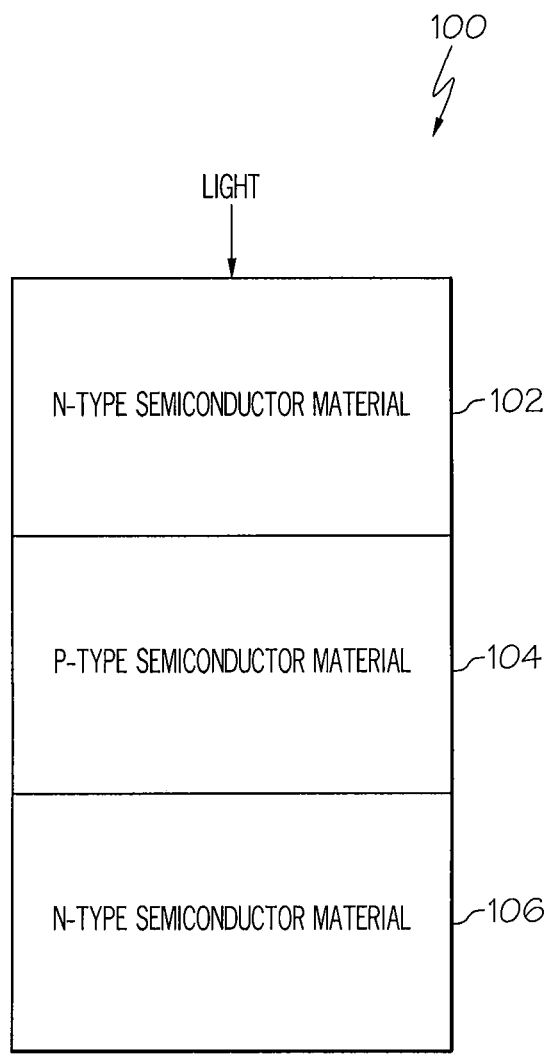
FIG. 1 is an example of a prior art multi-junction solar cell or photovoltaic cell for converting light energy into electrical energy or power.

The following detailed description of embodiments refers to the accompanying drawings, which illustrate specific embodiments of the disclosure. Other embodiments having different structures and operations do not depart from the scope of the present disclosure. Like reference numerals may refer to the same element or component in the different drawings.

As used herein, a solar cell may be a single junction solar cell or a multi-junction solar cell. A brief description of solar cells will be described to aid in understanding the present invention. Solar cells are semiconductor devices which are designed to generate electrical power when exposed to electromagnetic radiation, such as light and in particularly light generated by the sun. A solar cell may include a p type layer of semiconductor material and an n type layer of semiconductor material forming a p-n junction. The solar cell may also be a multi-junction solar cell including multiple p and n type layers of semiconductor material forming multiple p-n junctions. An example of a multi-junction solar cell 100 is illustrated in FIG. 1. Light enters the semiconductor material through the n layer or region and generates an electron-hole pair (EHP) in the material due to the photoelectric effect. The n region may be designed to be thin while the depletion region or area that forms between the n and p region may be thick compared to the n region. If the EHP is generated in the depletion region, an electric field that forms causes the electron and hole to drift apart. The result is a current through the device called the photocurrent. If the EHP is generated in the n or p regions, the electron and hole may drift in random directions and may or may not become part of the photocurrent.

In a single layer solar cell, much of the energy of the incident light may not be converted into electricity. If an incident photon has less energy than the energy bandgap of the semiconductor material or the energy needed to excite an electron from the conduction band to the valence band of the material, the photon cannot be absorbed because there is not enough energy to excite the electron from the conduction band to the valence band. Accordingly, light with less energy than the bandgap is not converted by the solar cell to electrical energy. If an incident photon has more energy than the bandgap of the semiconductor material, the excess energy will be converted into heat because the electron can only absorb the exact amount of energy required to move to the valence band.

Multi-junction solar cells may make better use of the solar spectrum by having multiple semiconductor layers with different bandgaps adapted to absorb different portions of the light spectrum or different wavelengths of light with different photon energy levels. Each layer of a multi-junction solar cell may be made from a different type of semiconductor material or doping of semiconductor material that absorbs a different portion of the light spectrum or range of wavelengths of light. An example of a multi-junction solar cell 100 is illustrated in FIG. 1. One form of a multi-junction solar cell is a 3 layer solar cell or a triple-junction solar cell as illustrated in FIG. 1. A top layer 102 of semiconductor material may include an n-type semiconductor material section 102a and a p-type semiconductor material section 102b and will have the largest bandgap so that only the most energetic photons are absorbed in this layer and converted to electricity. Less energetic photons will pass through the top layer 102 since they are not energetic enough to generate EHPs in the top layer of material 102 and may be absorbed by a middle layer of semiconductor material 104 which will have a smaller bandgap than the top section 102. A tunnel junction 103 is disposed between the top layer 102 and the middle layer 104. The middle layer 104 may include an n-type semiconductor material section 104a and a p-type semiconductor material section 104b. Similarly, a bottom layer 106 will have a smaller bandgap than the middle layer 104 to absorb any photons not energetic enough to generate an EHP in the top layer 102 or middle layer 104. Another tunnel junction 105 may be disposed between the middle layer 104 and the bottom layer 106. The bottom layer 106 may also include an n-type semiconductor material section 106a and a p-type semiconductor material section 106b. Each layer 102-106 going from the top layer 102 to the bottom layer 106 will have a smaller bandgap than the previous layer to absorb photons of varying energies for conversion to electrical power. Each layer 102-106 absorbs the photons that have energies greater than the bandgap of that layer and less than the bandgap of the higher layer. A more detailed description of solar cells and multi-junction solar cells is described in "Technology and Future III-V Multi-Junction Solar Cells" by Steven Lansel, School of Electrical and Computer Engineering, Georgia Institute of Technology, Apr. 21, 2005.

Figure 2:
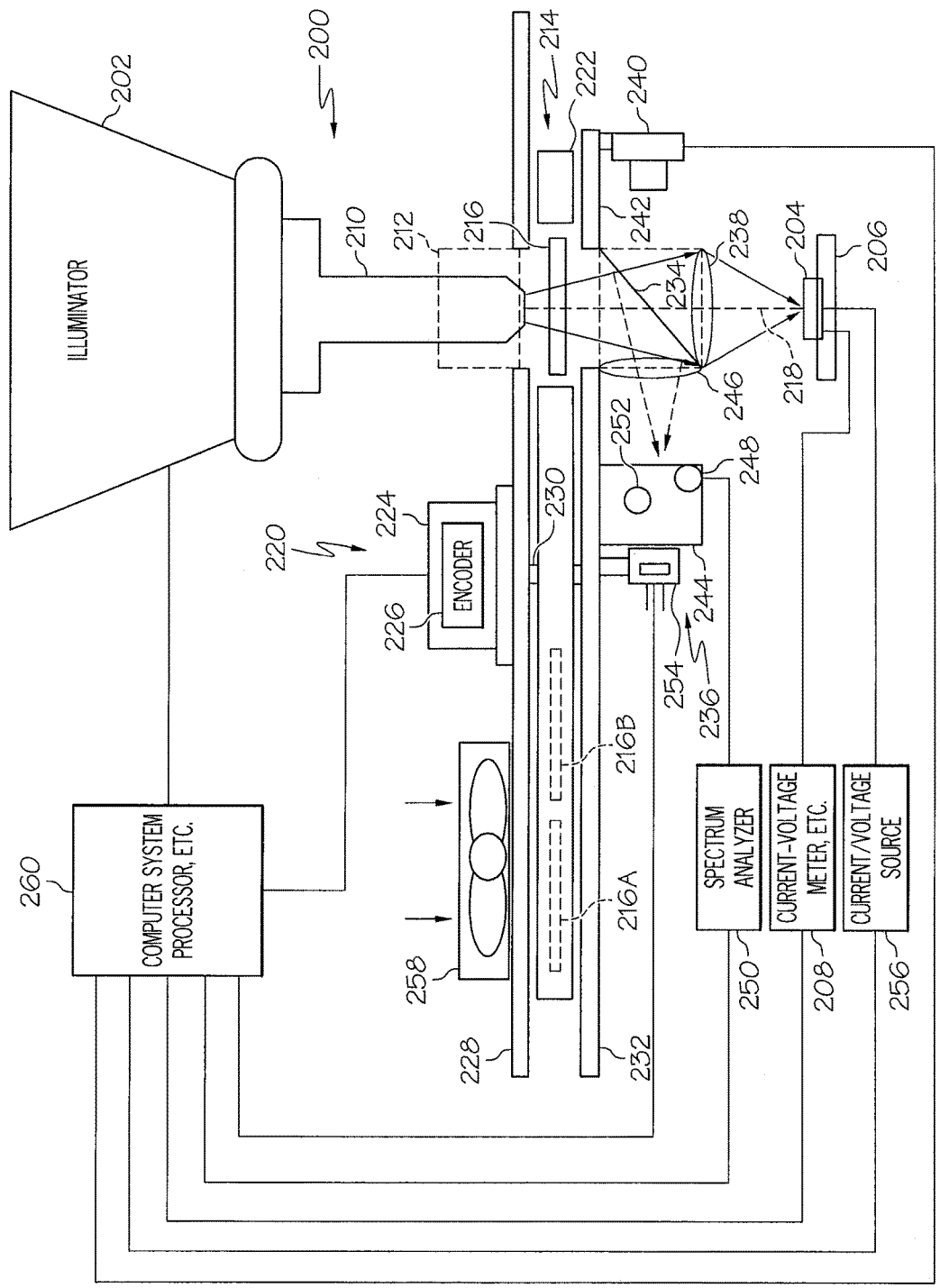
FIG. 2 is a schematic diagram of an example of a solar cell testing apparatus in accordance with an embodiment of the present disclosure.

FIG. 2 is a schematic diagram of an example of a solar cell testing apparatus 200 in accordance with an embodiment of the present disclosure. The solar cell testing apparatus 200 may include an illuminator 202 for directing light energy or photons on a solar cell 204 under test. The illuminator 202 may be a high intensity light source, such as an arc lamp or other light source capable of performing the test and valuations described herein. The solar cell 204 may be mounted in a movable fixture 206 that permits the solar cell 204 to be easily moved into a test location or position in the solar cell testing apparatus 200 and to be removed and replaced by another solar cell to be tested. The solar cell testing may be part of an automated process. The fixture 206 may also permit connection to equipment, such as a current-voltage meter 208, or other measurement equipment for measuring characteristics of the solar cell 204 under test. The fixture 206 may also permit an electrical current of a predetermined amperage from a current or voltage source 256 to be applied to the solar cell 204 for performing an electroluminescence test of the solar cell 204, as described in more detail herein. The electroluminescence test detects any light emission from the solar cell 204 that may be indicative of a defect in the solar cell 204.

The illuminator 202 may be coupled to a homogenizer 210 for conditioning the light from the illuminator 202 to be directed onto the solar cell 204. A light shield 212 and/or a douser in the illuminator 202 assembly may be used to control transmission of light from the illuminator 202 or homogenizer 210 to the solar cell.

The solar cell testing apparatus 200 may also include a device 214 for selectively positioning different filters of a multiplicity of filters 216 in an optical path 218 between the illuminator 202 and the solar cell 204 to at least one of measure performance of the solar cell 204 and detect any defects in the solar cell 204 based on the light characteristics produced by each filter 216. The device 214 for selectively positioning different filters of the multiplicity of filters 216 may include a mechanism 220 to position each of the multiplicity of filters 216 between the illuminator 202 and the solar cell 204. Performance characteristics of the solar cell 204 may be measured and tests performed under each of the different light conditions or characteristics and light intensity or energy levels incident on the solar cell caused by each the different filters 216 as described herein. The device 214 may include a rotatable filter wheel to 222 with the multiplicity of filters 216 mounted therein. An example of a multiple filter mechanism or rotatable filter wheel with a multiplicity of different filters mounted therein that may be used for the rotatable wheel 222 will be described with reference to FIG. 3. Any mechanism capable of moving the different filters into place for performing the different measurements and tests as described herein may be used.

The device 214 for selectively positioning different filters of the multiplicity of filters 216 in the optical path 218 between the illuminator 202 and the solar cell 204 may include a first set of filters 216a and a second set of filters and 216b. Each of the first set of filters 216a may be adapted to pass a predetermined percentage of intensity of the light energy from the illuminator 202 onto a solar cell 204 under test. The second set of filters 216b may each filter selected wavelengths or a selected spectrum of light from the illuminator 202 to direct the wavelengths or spectrum of light not filtered onto the solar cell 204 to test the solar cell under the different spectrums of light or ranges of wavelength to measure performance of the solar cell or to detect any defects in different layers of a multi-junction solar cell. Similar to that previously described, the different layers of a multi-junction solar cell may include different semiconductor materials to be reactive to or absorb different spectrums of light for generation of electrical power.

The rotatable filter wheel 222 may be rotated by a motor 224. The motor 224 may include an encoder 226 for determining a precise location or position of the rotatable filter wheel 222 and each filter 216 mounted in the wheel 222. The motor 224 and encoder 226 may accurately position each of the multiplicity of filters 216 in the optical path 218 between the illuminator 202 and the solar cell 204 for testing the solar cell 204 under the different light characteristics produced by each filter 216. The motor 224 may be mounted on a first mounting plate 228. The rotatable filter wheel 222 may be disposed on an opposite side of the first mounting plate 228 from the motor 224. A drive axle 230 may extend through the first mounting plate 228 and may be coupled to a hub of the filter wheel 222. And opposite end of the drive axle 230 may be rotatably coupled to a second mounting plate 232 on an opposite side of the filter wheel 222 from the first mounting plate 228. Accordingly, the filter wheel 222 may be disposed between the first mounting plate 228 and the second mounting plate 232. An aperture may be formed in each of the first mounting plate 228 and the second mounting plate 232 in alignment with a currently selected filter 216 of the filter wheel 222 to permit the light from the illuminator 202 to pass through the selected filter 216 currently positioned in the optical path 218 between the illuminator 202 and the solar cell 204 being tested.

The solar cell testing apparatus 200 may also include a beam splitter 234 for directing a predetermined portion of the light energy from the illuminator 202 and from a selected filter 216 of the multiplicity of filters onto the solar cell 204 for testing the solar cell 204. The beam splitter may also direct another predetermined portion of light energy to an apparatus 236 for measuring characteristics of the light from the selected filter 216 of the multiplicity of filters currently positioned in the optical path 218 between the illuminator 202 and solar cell 204. An imaging lens 238 may be disposed between the beam splitter 234 and the solar cell 204 being tested to focus the light on the solar cell 204. The imaging lens 238 may also facilitate capturing images of the solar cell 204 by a camera 240 when performing an electroluminescence test of the solar cell 204, as described in more detail herein. The electroluminescence test may be performed by positioning a light blocking filter mounted in the filter wheel 222 between the illuminator 202 and the solar cell 204. The camera 240 may be mounted to an opposite side 242 of the second mounting plate 230 from the rotatable filter wheel 222.

The apparatus 236 for measuring characteristics of the light from the selected filter 216 may include an integrating sphere 244. The integrating sphere 244 may be mounted to the opposite side 242 of the second mounting plate 232 from the filter wheel 222. The integrating sphere 244 permits measurements of light characteristics that are independent on the angle of incidence of the light. Another or second imaging lens 246 may be disposed proximate to the beam splitter 234 and between the beam splitter 234 and the imaging sphere 244. The second imaging lens 246 may focus the light from the beam splitter 234 onto the imaging sphere 244.

The apparatus 236 for measuring characteristics of the light from the selected filter 216 may also includes a port 248 for a spectrum analyzer 250. The spectrum analyzer 250 may measure the spectrum of light which is being transmitted by the filter 216 currently disposed between the illuminator 202 and the solar cell 204.

The apparatus 236 for measuring the characteristics of the light from the current filter 216 may also include ports for isotopes 252. Additional ports may also be provided that can simultaneously record other signals such as various Isotype signals (top, middle and bottom) and full power signals.

The apparatus 236 for measuring the characteristics of the light from the current filter 216 may also include a light intensity detector 254 to detect or measure the intensity or candle power of the light being passed by the current filter 216 of the rotatable filter wheel 222. The intensity detector 254 may be a silicon (Si) detector or other light intensity detector.

The solar cell testing apparatus 200 may also include a current voltage source 256 to apply an electrical current of a predetermined amperage to the solar cell 204 for performing and electroluminescence test of the solar cell when a block filter mounted in the rotatable filter wheel 222 is positioned in the optical path 218.

The solar cell testing apparatus 200 may also include a cooling fan or fans 258 to cool the apparatus 200 from heat resulting from operation of the illuminator 202.

A computer system or processor 260 may control operation of the solar cell testing apparatus 200. The processor 260 may be coupled to the illuminator 202 and the motor 224 and encoder 226. The processor 260 may control operation of the illuminator 202 and rotation of the filter wheel 222 to position selected filters 216 in the optical path 218 for testing the solar cell 204 under the different light characteristics provided by the different filters 216 of the filter wheel 222

The processor 260 may also be coupled to the light intensity detector 254 to record the intensity of light from the filters 216. The processor 260 may additionally be connected to the current-voltage meter or other measurement equipment for recording the current-voltage curves and other parameters of the solar cell 204. The processor 260 may also be connected to the current/voltage source 256 to control operation of the current/voltage source 256 during the electroluminescence testing of the solar cell 204. The processor 260 may further be connected to the camera 240 and images of the solar cell 204 captured by the camera 240 during electroluminescence testing may be stored and processed by the processor 260.

Figure 3:
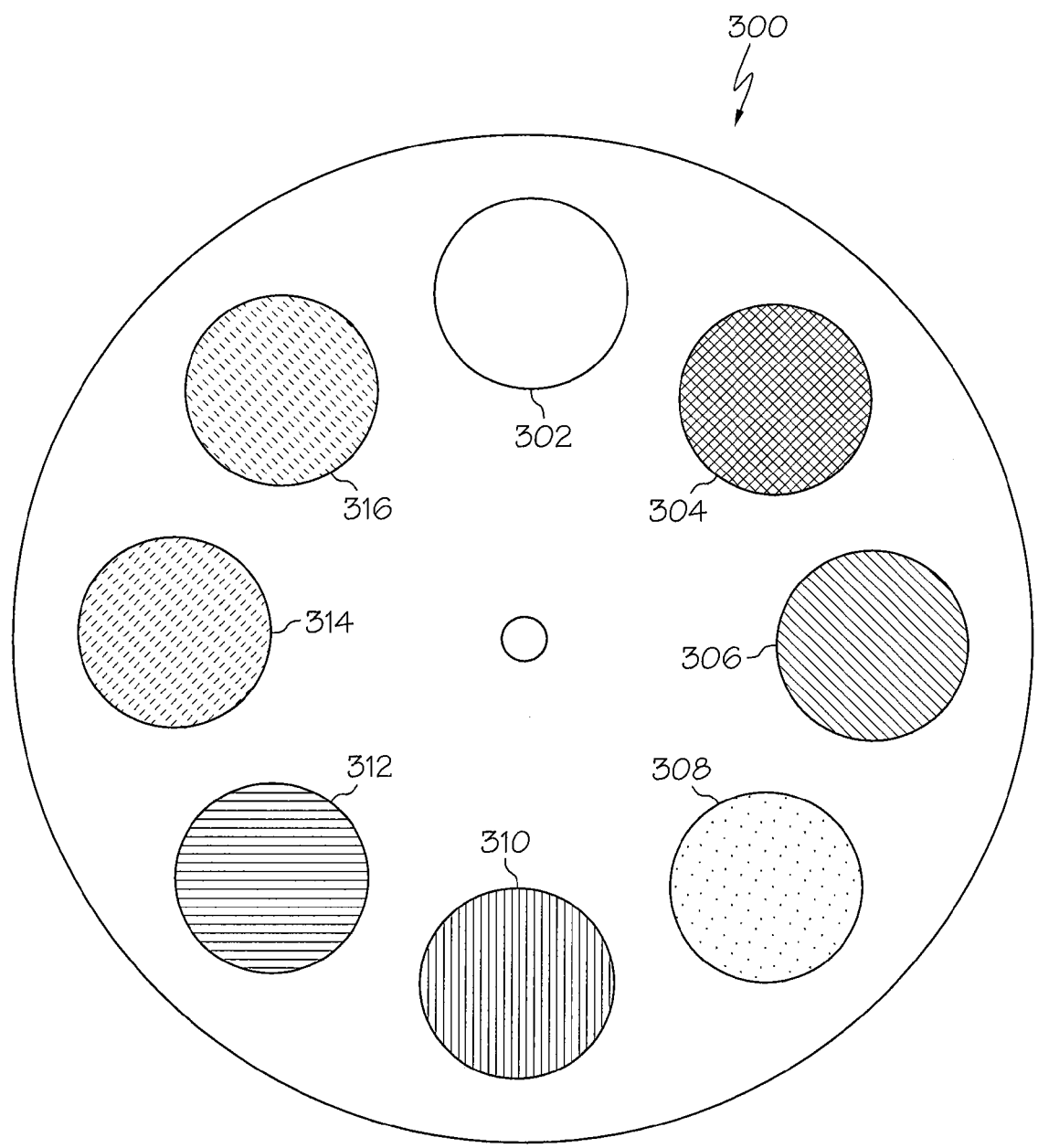
FIG. 3 is an example of a multiple filter mechanism for a solar cell testing apparatus in accordance with an embodiment of the present disclosure.

FIG. 3 is an example of a multiple filter mechanism or filter wheel 300 with a multiplicity of different filters 302-316 mounted therein for use with a solar cell testing apparatus in accordance with an embodiment of the present disclosure. The filter wheel 300 may be used for the filter wheel 222 and FIG. 2. Each of the multiplicity of filters 302-316 may be positioned circumferential about a hub 318 of the wheel 304 for positioning each of the filters 302-316 in the optical path 218 (FIG. 2) between the illuminator 202 and the solar cell 204 as the wheel 300 is rotated about the hub 318 by the motor 224.

A first filter or aperture 302 of the filter wheel 300 in a first position or location on the filter wheel 300 may transmit or pass 100 percent or all of the light intensity from the illuminator to the solar cell. The first filter 302 may be referred to as a 100 percent filter. A second filter or aperture 304 in a second position or location on the filter wheel 300 may transmit or pass about 66 percent of the light intensity from the illuminator to the solar cell. The second filter 304 may be referred to as a 66 percent filter. A third filter or aperture 306 in a third position or location on the filter wheel 300 may transmit or pass about 33 percent of the light intensity from the illuminator to the solar cell. The third filter 304 may be referred to as a 33 percent filter. A fourth filter 308 or aperture in a fourth position or location on the filter wheel 300 may transmit or pass about 10 percent of the light intensity from the illuminator to the solar cell. The fourth filter 308 may be referred to as a 10 percent filter. The filters 302-308 may define a first set of filters which are each adapted for passing a predetermined percentage of intensity of light from the illuminator onto the solar cell under test.

A fifth filter 310 or aperture in a fifth position or location of the filter wheel 300 may be a blue filter to pass a blue starved spectrum of light from the illuminator onto the solar cell for testing. The blue starved spectrum of light may be light with substantially all or most of the blue spectrum removed or blue portion of the frequency range or bandwidth of light being filtered or removed. A sixth filter 312 or aperture in a sixth position or location of the filter wheel 300 may be a red filter to pass a red starved spectrum of light from the illuminator onto the solar cell under test. The red starved spectrum of light may be light with substantially all or most of the red spectrum or red portion of the frequency range or bandwidth of light being filtered or removed. A seventh filter 314 or aperture in a seventh position or location of the filter wheel 300 may be an infrared filter to pass an infrared starved spectrum of light from the illuminator onto the solar cell. The infrared spectrum of light may be light with substantially all or most of the infrared frequency range or bandwidth of light removed or filtered. The filters 310-314 may define a second set of filters for testing the solar cell under different spectrums of light. As previously discussed in a multi-junction solar cell different layers of the solar cell will be reactive or absorb different spectrums of light for generating electrical power. Measurements performed when the different spectrums of light are transmitted by the different filters 310-314 onto the solar cell permit determination of the amount or level of electrical power the solar cell under test is capable of generating when he each different spectrum of light is incident upon the solar cell.

The filter wheel 300 may also include a light blocking filter 316 to prevent light from being incident upon the solar cell from the illuminator. The light blocking filter 316 may be used for performing an electroluminescence test of the solar cell to detect light emission from the solar cell in response to an electric current of a predetermined amperage being applied to the solar cell by a current source, such as current source 256 in FIG. 2. As previously discussed, a camera, such as camera 240 in FIG. 2, may capture an image or images of the solar cell in response to the electrical current being applied to the solar cell to detect light emission from the solar cell indicating the solar cell may have a defect. The image of the solar cell may be split into beams of different wavelengths of light energy corresponding to different layers of a multi-junction solar cell. The image of the solar cell may be split into the beams of different wavelengths by a beam splitter or similar device.

Figure 4A:
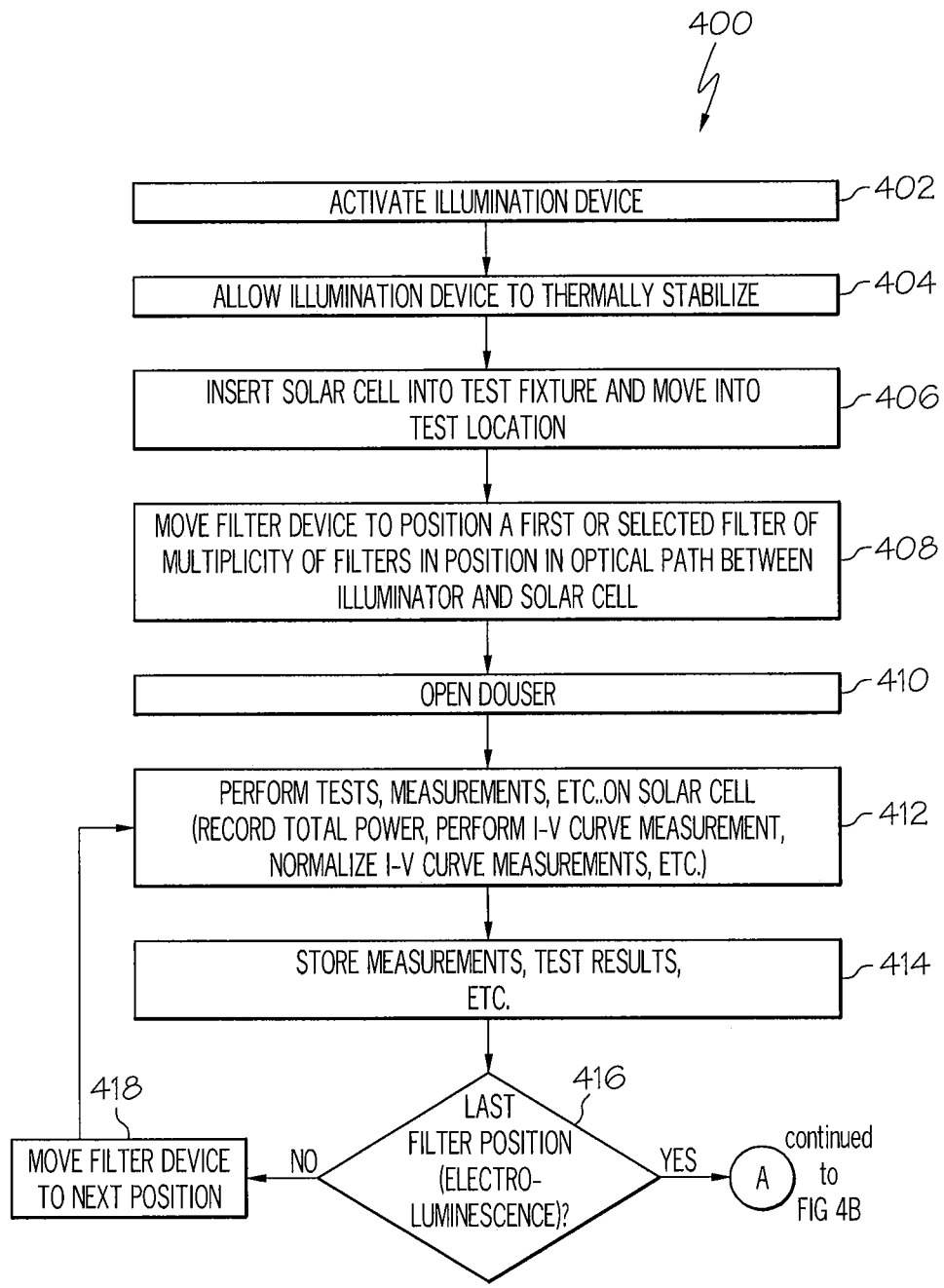
FIGS. 4A and 4B (collectively FIG. 4) are a flow chart of an example of a method for testing solar cells in accordance with an embodiment of the present disclosure.
Figure 4B:
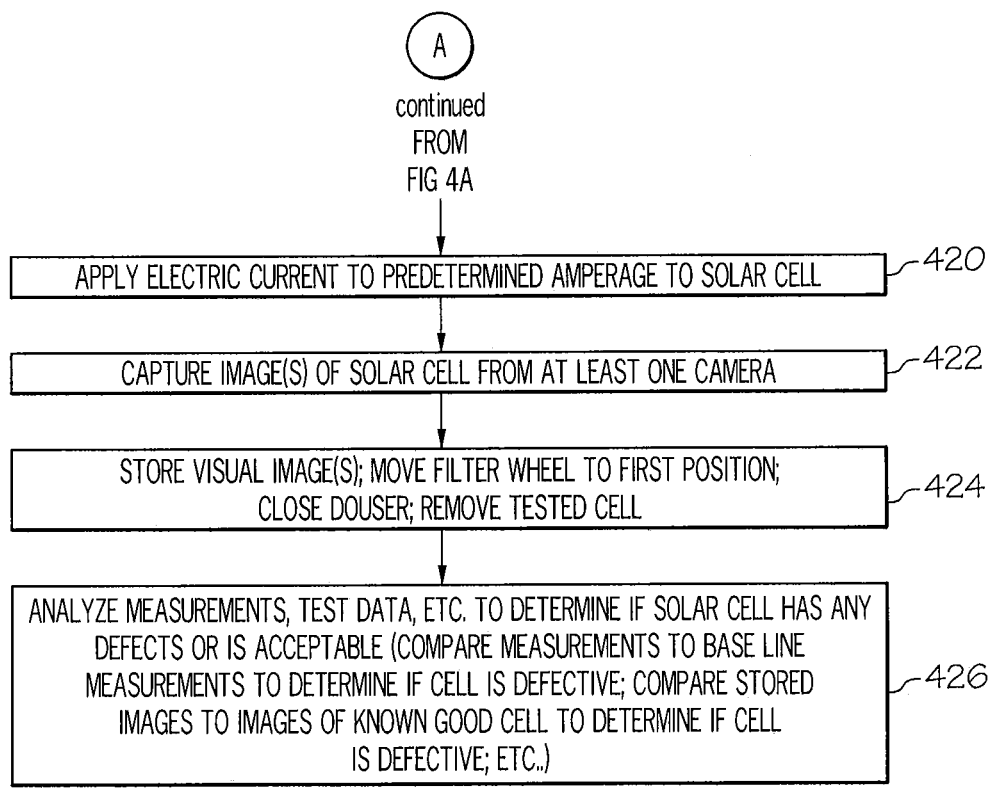

FIGS. 4A and 4B (collectively FIG. 4) are a flow chart of an example of a method 400 for testing solar cells in accordance with an embodiment of the present disclosure. The method 400 may be embodied in and/or performed by the apparatus 200 and FIG. 2. In block 402, and illumination device, such as for example illumination device 202 in FIG. 2 may be activated. In block 404, the illumination device may be allowed to thermally stabilize.

In block 406, a solar cell may be inserted into a test fixture and moved into a test location. In block 408, a filter device may be moved or operated to position a first filter or a selected filter of a multiplicity of filters in position in an optical path between the illuminator and the solar cell. The filter device may be similar to the device 214 in FIG. 2 or the filter wheel 300 and FIG. 3.

In block 410, a douser or light shield may be opened to allow light from the illuminator to be filtered by the selected filter of the multiplicity of filters and to be directed from the filter onto the solar cell. As previously discussed, the light may be split by a beam splitter to direct a predetermined portion of the filtered light onto the solar cell and to direct another predetermined portion of the light to an apparatus for measuring characteristics of light from each of the multiplicity of filters.

Figure 5:
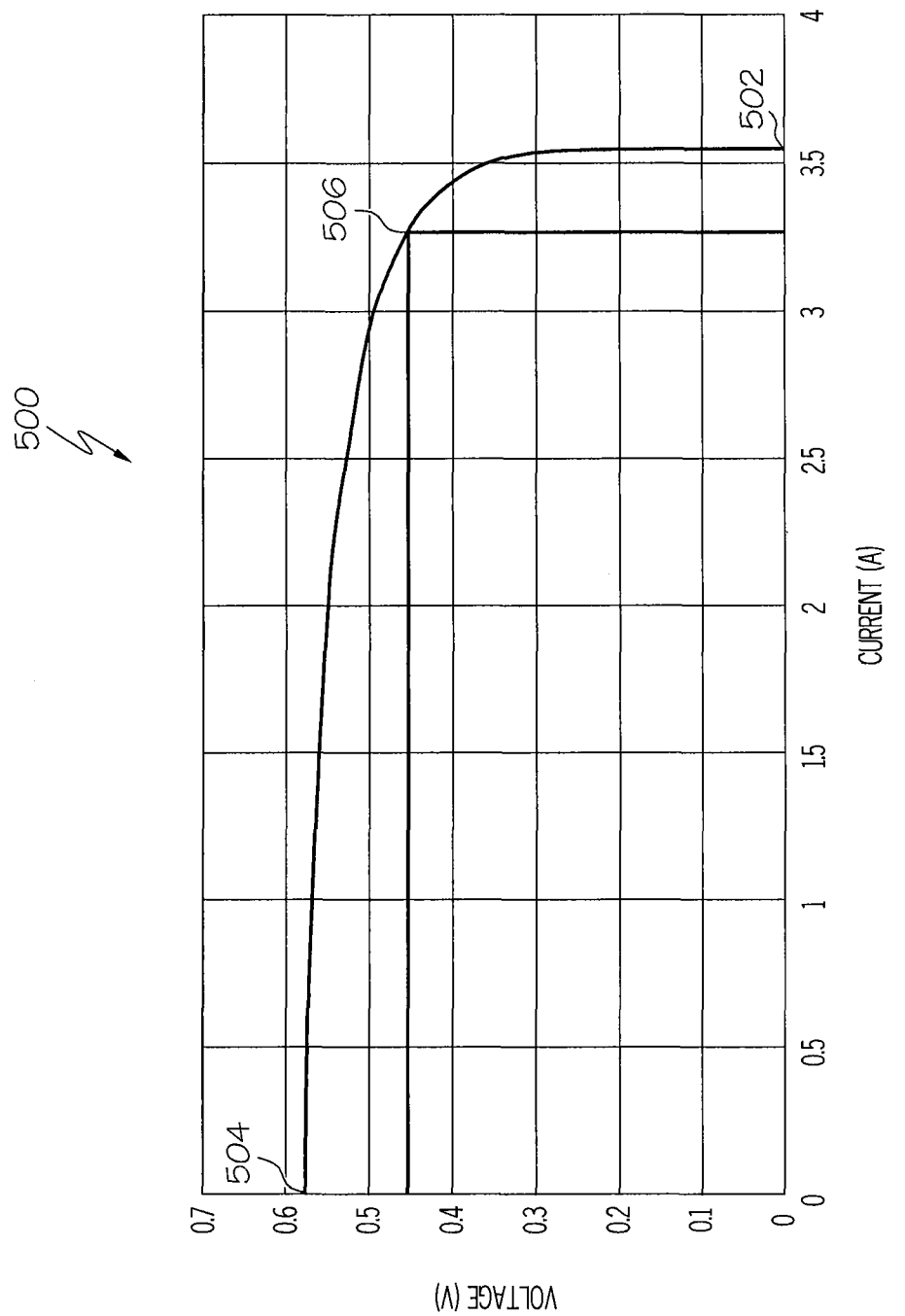
FIG. 5 is an example of a current versus voltage (I-V) curve for a solar cell in accordance with an embodiment of the present disclosure.

In block 412, tests and measurements may be performed on the solar cell to at least one of measure performance of the solar cell or to detect any defects. Measurements which may be performed may include recording an intensity or power of the light energy, measuring a total electrical power generated by the solar cell, performing a current versus voltage (I-V) curve measurement. The I-V curve measurement may be normalized for comparison with other I-V measurements. An example of an I-V curve 500 is illustrated in FIG. 5.

In block 414, the measurements and test results may be stored for analysis with results from other filters to measure performance or detect any defects in the solar cell. In block 416 a determination may be made whether the current filter is a last filter or last filter position of the filter wheel or if the current wheel is the light blocking filter. If the current filter is the last filter or filter position of the multiplicity of filters or is the light blocking filter, the method 400 may advance to block 420 and an electroluminescence test of the solar cell may be performed. If the current filter is not the last filter or the light blocking filter, the method 400 may advance to block 418 and the filter device or filter wheel may be moved to the next position to place the next filter in the optical path between the illumination device and the solar cell. The method 400 may then cycle through each of the filters or filter positions to test the solar cell under the various light characteristics as described herein.

Blocks 412-418 involve filtering light directed onto the solar cell by each of the multiplicity of filters and storing measurements and test results for analysis to measure performance and/or detect any defects in the solar cell. Filtering the light may include positioning each of a first set of filters in the optical path between the illuminator and the solar cell. Each filter of the first set of filters may be adapted to pass a predetermined percentage of intensity of light or light energy to test the solar cell under different levels of intensity of light or energy. Filtering the light may also include positioning each of a second set of filters in the optical path. Each filter of the second set of filters may be adapted to test the solar cell under different spectrums of light to test different layers of a multi-layer solar cell. Filtering the light may also include positioning a light blocking filter in the optical path to perform an electroluminescence test of the solar cell to detect light emission from the solar cell.

In block 420 with the light blocking filter in the optical path, an electric current of a predetermined amperage may be applied to the solar cell. In block 422, an image or images of the solar cell may be captured from at least one camera or other imaging device. In block 424, the visual image or images of the solar cell may be stored. The light shield may be closed and the tested solar cell may be removed. The filter wheel may be moved to the first position in preparation for testing the next solar cell to be inserted into the testing apparatus.

In block 426, the measurements and test results may be analyzed to determine if the solar cell has any defects or is acceptable. Measurements may be compared to baseline measurements to determine if the cell is defective. Stored images from the electroluminescence test may be compared to images of known good solar cells to determine if the cell is defective. Examples of the parameters that may be determined from the measurements and test data to evaluate the performance of the solar cell under test may include the short-circuit current ($J_{SC}$), the open circuit voltage ($V_{OC}$), the power point, the fill factor (FF), the quantum efficiency and the overall efficiency. The short-circuit current ($J_{SC}$) is the current of a solar cell when the top and bottom (negative and positive leads) are connected with a short circuit. The short circuit current is the horizontal intercept 502 of the I-V curve in FIG. 5.

The open circuit voltage ($V_{OC}$) is the voltage between the top and bottom of a solar cell. The open circuit voltage is the vertical intercept 504 of the I-V curve in FIG. 5.

The power point is the point on the I-V curve of a solar cell at ($J_{PP}$, $V_{PP}$) that generates the maximum amount of power for the device. The power point encloses the most amount of area in the first quadrant where vertical and horizontal lines are drawn from the power point. This represents power since the area is equivalent to the current times voltage of the cell. The power point is shown and FIG. 5 by reference numeral 506.

The fill factor (FF) is a percentage given by equation 1 that describes how close the I-V curve of the solar cell resembles a perfect rectangle, which represents the ideal solar cell.

$$\text{Fill Factor} = \frac{V_{PP} * J_{PP}}{V_{OC} * J_{SC}} \qquad \text{Equation 1}$$

Quantum efficiency is the number of EHP's that are created and collected divided by the number of incident photons. This is a percentage since each photon can produce at most one EHP.

Overall efficiency is the percentage of incident electromagnetic radiation that is converted to electrical power. Often the overall efficiency for a given solar cell depends on many factors including the temperature and amount of incident radiation.

Figure 6:
FIG. 6 is an example of a table of different positions of a multiple filter mechanism for testing a solar cell in accordance with an embodiment of the present disclosure.

FIG. 6 is an example of a table 600 of different positions of a multiple filter mechanism for testing a solar cell in accordance with an embodiment of the present disclosure. Each filter or filter location may correspond to a different test which may be performed on the solar cell when the respective filter is positioned in the optical path between the illuminator and the solar cell. For example, filter 1 or filter location 1 may correspond to a first predetermined percentage of power or in this example a 100 percent filter or filter that transmits full power to the solar cell.

Filter 2 or filter location 2 may correspond to a second predetermined percentage of power or in this example a 50 percent filter or filter adapted to transmit 50 percent of the power or light intensity to the solar cell. Filter 3 or filter location 3 may correspond to another predetermined percentage of power or a filter that transmits 10 percent of the power to the solar cell.

Filter 4 or filter location 4 may correspond to a top starved test in which the filter includes characteristics to test the solar cell by filtering a spectrum of light corresponding to the spectrum of light to which the top layer of semiconductor material of the solar cell is reactive or in other words filters the spectrum of light containing photons that would be absorbed by the top layer of the solar cell.

Filter 5 or filter location 5 may correspond to a middle starved test in which the filter includes light filtering characteristics to test the solar cell by filtering a spectrum of light corresponding to the spectrum of light to which the middle layer of the solar cell is reactive.

Filter 6 or filter location 6 may correspond to a bottom starved test in which the filter includes characteristics to test the solar cell by filtering the spectrum of light to which the bottom layer of the solar cell is reactive.

Filter 7 or filter location 7 may correspond to a dark I-V curve test in which the filter includes characteristics to test the solar cell by filtering all the light from the illuminator to measure a dark current versus voltage characteristic curve.

Filter 8 or filter location 8 may correspond to an electroluminescence test in which the filter includes light filtering characteristics to perform an electroluminescence test on the solar cell similar to that previously discussed.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Although specific embodiments have been illustrated and described herein, those of ordinary skill in the art appreciate that any arrangement which is calculated to achieve the same purpose may be substituted for the specific embodiments shown and that the embodiments herein have other applications in other environments. This application is intended to cover any adaptations or variations of the present disclosure. The following claims are in no way intended to limit the scope of the disclosure to the specific embodiments described herein.

What is claimed is:
1. A solar cell testing apparatus, comprising:
an illuminator for directing light energy on a solar cell under test; and
a device for selectively positioning different filters of a multiplicity of filters in an optical path between the illuminator and the solar cell under test to at least one of measure performance and detect any defects in the solar cell, the multiplicity of filters comprising a first set of filters, each filter of the first set of filters being adapted for passing a different predetermined percentage of intensity of the light energy from the illuminator onto the solar cell under test, and a second set of filters, each filter of the second set of filters being configured for testing the solar cell under a different spectrum of light, wherein the device for selectively positioning the different filters comprises:
a rotatable wheel, each of the multiplicity of filters being positioned circumferentially about a hub of the rotatable wheel for positioning each of the filters between the illuminator and the solar cell as the rotatable wheel is rotated about the hub; and
a motor including an encoder and a drive axle, the drive axle of the motor being directly connected to the hub of the rotatable wheel to rotate the rotatable wheel for positioning each of the filters sequentially between the illuminator and the solar cell.
2. The solar cell testing apparatus of claim 1, wherein the multiplicity of filters further comprises a light blocking filter to perform an electroluminescence test of the solar cell to detect light emission from the solar cell in response to an electric current of a predetermined amperage being applied to the solar cell.

3. The solar cell testing apparatus of claim 2, further comprising:
   a current source to apply the electrical current to the solar cell when the light blocking filter is disposed between the illuminator and the solar cell;
   a camera to capture an image of the solar cell in response to the electrical current being applied to the solar cell to detect light emission from the solar cell; and
   a beam splitter to split the image of the solar cell into beams of different wavelengths of light energy corresponding to different layers of the solar cell, wherein the solar cell is a multiple junction solar cell.

4. The solar cell testing apparatus of claim 1, wherein the first set of filters comprises:
   a 100 percent filter to pass all of the light intensity from the illuminator to the solar cell;
   a 66 percent filter to pass 66 percent of the light intensity from the illuminator to the solar cell;
   a 33 percent filter to pass 33 percent of the light intensity from the illuminator to the solar cell; and
   a 10 percent filter to pass 10 percent of the light intensity from the illuminator to the solar cell.

5. The solar cell testing apparatus of claim 1, wherein the second set of filters comprises:
   a red filter to pass a red starved spectrum of light from the illuminator onto the solar cell;
   a blue filter to pass a blue starved spectrum of light from the illuminator onto the solar cell; and
   an infrared filter to pass an infrared starved spectrum of light from the illuminator onto the solar cell.

6. The solar cell testing apparatus of claim 1, further comprising:
   a beam splitter for receiving the light energy from the illuminator filtered by one of the multiple filters currently in position between the illuminator and the solar cell;
   an integrating sphere, wherein the beam splitter directs a portion of the light energy from the illuminator to the integrating sphere and directs another portion of the light energy to the solar cell; and
   a spectrum analyzer coupled to the integrating sphere to analyze the portion of the light energy received.

7. The solar testing apparatus of claim 1, further comprising:
   a light detector for measuring an intensity level of the light from the illuminator; and
   a device for measuring a current versus voltage curve (I-V curve) of the solar cell under each filter.

8. The solar cell testing apparatus of claim 1, wherein the device for selectively positioning different filters of the multiplicity of filters comprises a mechanism to position each of the multiplicity of filters between the illuminator and the solar cell for measuring the performance characteristics of the solar cell for each of the multiple filters.

9. The solar cell testing apparatus of claim 1, further comprising a light shield to control transmission of light from the illuminator to the solar cell.

10. The solar cell testing apparatus of claim 1, further comprising:
    a first mounting plate;
    a second mounting plate, wherein the single rotatable wheel is disposed between the first mounting plate and the second mounting plate;
    an aperture formed in each of the first mounting plate and the second mounting plate in alignment with a currently selected filter of the multiplicity of filters, the apertures permitting light from the illuminator to pass through the currently selected filter positioned in the optical path between the illuminator and the solar cell under test.

11. The solar cell testing apparatus of claim 10, wherein the motor is mounted to the first mounting plate, the drive axle of the motor extending through the first mounting plate and being directly connected to the hub of the rotatable wheel for positioning each of the filters of the multiplicity of filters in the optical path for testing the solar cell.

12. The solar cell testing apparatus of claim 10, further comprising an apparatus for measuring characteristics of the light from each filter of the multiplicity of filters when positioned in the optical path for testing the solar cell, the apparatus for measuring characteristics of the light being mounted on a side of the second mounting plate opposite the rotatable wheel.

13. A solar cell testing apparatus, comprising:
    an illuminator;
    a device for selectively positioning different filters of a multiplicity of filters in an optical path between the illuminator and a solar cell under test, wherein the device for selectively positioning the different filters comprises:
      a rotatable wheel, each of the multiplicity of filters being positioned circumferentially about a hub of the rotatable wheel for positioning each of the filters between the illuminator and the solar cell as the rotatable wheel is rotated about the hub, the multiplicity of filters comprising a first set of filters, each filter of the first set of being configured for passing a different predetermined percentage of intensity of the light energy from the illuminator onto the solar cell under test, and a second set of filters, each filter of the second set of filters being configured for testing the solar cell under a different spectrum of light; and
      a motor including an encoder and a drive axle, the drive axle of the motor being directly connected to the hub of the rotatable wheel to rotate the rotatable wheel for positioning each of the filters sequentially between the illuminator and the solar cell; and
    a beam splitter for directing a predetermined portion of the light from a selected filter of the multiplicity of filters onto the solar cell to at least one of measure performance and detect any defects in the solar cell, and for directing another predetermined portion of the light energy to an apparatus for measuring characteristics of the light from the selected filter of the multiplicity of filters positioned in the optical path between the illuminator and the solar cell.

14. The solar cell testing apparatus of claim 13, further comprising a device for at least one of measuring performance characteristics of the solar cell and to detect any defects in the solar cell.

15. The solar cell testing apparatus of claim 13, wherein the solar cell comprises a top layer of semiconductor material reactive to a first spectrum of light, a middle layer of semiconductor material reactive to a second spectrum of light and a bottom layer of semiconductor material reactive to a third spectrum of light, and wherein the device for selectively positioning different filters of the multiplicity of filters comprises:
    a first filter position corresponding to a first filter to pass 100 percent of the light energy to test the solar cell under full power;
    a second filter position including a second filter to test the solar cell under a predetermined percentage of power corresponding to a predetermined percentage of light energy passed by the second filter;

a third filter position including a third filter to test the solar cell by filtering a spectrum of light corresponding to the first spectrum of light to which the top layer of semiconductor material of the solar cell is reactive;

a fourth filter position including a fourth filter to test the solar cell by filtering a spectrum of light corresponding to the second spectrum of light to which the middle layer of semiconductor material of the solar cell is reactive;

a fifth filter position including a fifth filter to test the solar cell by filtering a spectrum of light corresponding to the third spectrum of light to which the bottom layer of semiconductor material of the solar cell is reactive;

a sixth filter position including a sixth filter to test the solar cell by filter the light from the illuminator to measure a current-voltage characteristic curve of the solar cell under a dark condition or without light being received by the solar cell; and a seventh filter position including a seventh filter to block light to perform an electroluminescence test on the solar cell.

16. The solar cell testing apparatus of claim 13, wherein the multiplicity of filters comprises:

a light blocking filter to perform an electroluminescence test of the solar cell to detect light emission from the solar cell in response to an electric current of a predetermined amperage being applied to the solar cell.

17. The solar cell testing apparatus of claim 13, wherein the first set of filters comprises:

a 100 percent filter to pass all of the light intensity from the illuminator to the solar cell;

a 66 percent filter to pass about 66 percent of the light intensity from the illuminator to the solar cell;

a 33 percent filter to pass about 33 percent of the light intensity from the illuminator to the solar cell; and a 10 percent filter to pass about 10 percent of the light intensity from the illuminator to the solar cell.

18. The solar cell testing apparatus of claim 13, wherein the second set of filters comprises:

a red filter to pass a red starved spectrum of light from the illuminator onto the solar cell;

a blue filter to pass a blue starved spectrum of light from the illuminator onto the solar cell; and an infrared filter to pass an infrared starved spectrum of light from the illuminator onto the solar cell.

19. A method for testing a solar cell, comprising:

filtering light directed onto the solar cell by each of a multiplicity of filters to at least one of measure performance and detect any defects in the solar cell, wherein filtering the light comprises:

positioning each filter of a first set of filters in an optical path between an illuminator and the solar cell, each filter of the first set of filters being adapted to pass a different predetermined percentage of intensity of light energy to test the solar cell under different levels of intensity of light; and positioning each of a second set of filters in the optical path between the illuminator and the solar cell, each filter of the second set of filters being adapted to test the solar cell under a different spectrum of light, wherein positioning each filter of the multiplicity of filters comprises rotating a rotatable wheel, each of the multiplicity of filters being positioned circumferentially about a hub of the rotatable wheel for positioning each of the filters between the illuminator and the solar cell as the rotatable wheel is rotated about the hub, the rotatable wheel being positioned by a motor including an encoder and a drive axle, the drive axle of the motor being directly connected to the hub of the rotatable wheel to rotate the rotatable wheel for positioning each of the filters sequentially between the illuminator and the solar cell; and splitting the light to direct a predetermined portion of the filtered light onto the solar cell and to direct another predetermined portion of the light to an apparatus for measuring characteristics of the light from each of the multiplicity of filters.

20. The method of claim 19, wherein filtering the light comprises:

positioning a light blocking filter in the optical path to perform an electroluminescence test of the solar cell to detect light emission from the solar cell in response to an electric current of a predetermined amperage being applied to the solar cell.

21. The method of claim 19, wherein the solar cell comprises a top layer of semiconductor material reactive to a first spectrum of light, a middle layer of semiconductor material reactive to a second spectrum of light and a bottom layer of semiconductor material reactive to a third spectrum of light, and wherein filtering the light comprises:

positioning a first filter adapted to pass 100 percent of the light energy to test the solar cell under full power;

positioning a second filter including light filtering characteristics to test the solar cell under a predetermined percentage of power corresponding to a predetermined percentage of light energy passed by the second filter;

positioning a third filter including light filtering characteristics to test the solar cell by filtering a spectrum of light corresponding to the first spectrum of light to which the top layer of semiconductor material of the solar cell is reactive;

positioning a fourth filter including light filtering characteristics to test the solar cell by filtering a spectrum of light corresponding to the second spectrum of light to which the middle layer of semiconductor material of the solar cell is reactive;

positioning a fifth filter position including light filtering characteristics to test the solar cell by filtering a spectrum of light corresponding to the third spectrum of light to which the bottom layer of semiconductor material of the solar cell is reactive;

positioning a sixth filter including light filtering characteristics to test the solar cell by filter the light from the illuminator to measure a dark current-voltage characteristic curve; and positioning a seventh filter position including light filtering characteristics to perform an electroluminescence test on the solar cell.

\* \* \* \* \*